(12) United States Patent
Alfoqaha et al.

(10) Patent No.: US 8,135,479 B2
(45) Date of Patent: Mar. 13, 2012

(54) SENSOR ASSEMBLIES FOR IMPLANTABLE MEDICAL ELECTRICAL LEADS

(75) Inventors: Arshad A. Alfoqaha, Eden Prairie, MN (US); Kris A. Peterson, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 994 days.

(21) Appl. No.: 12/107,987

(22) Filed: Apr. 23, 2008

(65) Prior Publication Data

US 2009/0270707 A1    Oct. 29, 2009

(51) Int. Cl.
*A61N 1/00* (2006.01)
*G01L 9/12* (2006.01)

(52) U.S. Cl. .................... 607/122; 607/116; 73/718

(58) Field of Classification Search .............. 600/372, 600/374, 377, 381, 486, 488; 607/9.17, 17, 607/116, 122–126; 73/718, 724, 866.5
See application file for complete search history.

(56) References Cited

U.S. PATENT DOCUMENTS

| | | | |
|---|---|---|---|
| 4,815,469 A * | 3/1989 | Cohen et al. ................ | 600/333 |
| 4,967,755 A | 11/1990 | Pohndorf | |
| 5,222,506 A | 6/1993 | Patrick et al. | |
| 5,314,458 A * | 5/1994 | Najafi et al. ................ | 607/116 |
| 5,324,326 A | 6/1994 | Lubin | |
| 5,490,323 A * | 2/1996 | Thacker et al. .............. | 29/825 |
| 5,535,752 A | 7/1996 | Halperin et al. | |
| 6,221,024 B1 * | 4/2001 | Miesel ...................... | 600/486 |
| 7,231,829 B2 | 6/2007 | Schugt | |
| 7,286,884 B2 * | 10/2007 | Marshall et al. .............. | 607/122 |
| 7,418,868 B1 * | 9/2008 | Karicherla et al. ............ | 73/700 |
| 2003/0139794 A1 * | 7/2003 | Jenney et al. ................ | 607/122 |
| 2008/0269623 A1 * | 10/2008 | Ruben ...................... | 600/488 |

OTHER PUBLICATIONS

International Search Report, PCT/US2009/040088, 4 pages.

* cited by examiner

*Primary Examiner* — Linda Dvorak
*Assistant Examiner* — Brian M Antiskay
(74) *Attorney, Agent, or Firm* — Reed A. Duthler; Stephen W. Bauer

(57) ABSTRACT

A sensor assembly, which may be incorporated by a medical electrical lead, includes an insulative body, formed from a biocompatible plastic, and a sensor mounted on a mounting surface of the insulative body. The mounting surface extends distally from a proximal portion of the insulative body in which first and second conductive inserts extend, being spaced apart and isolated from one another. The sensor is coupled to each of the first and second conductive inserts, and the first conductive insert includes a conductor-coupling end extending proximally from the proximal portion of the insulative body. The sensor assembly may further include an electrode extending around the sensor and the insulative body, wherein the electrode includes an aperture approximately aligned with an active surface of the sensor to expose the active surface. A mounting platform assembly for the sensor assembly may include the conductive inserts and the insulative body.

26 Claims, 5 Drawing Sheets

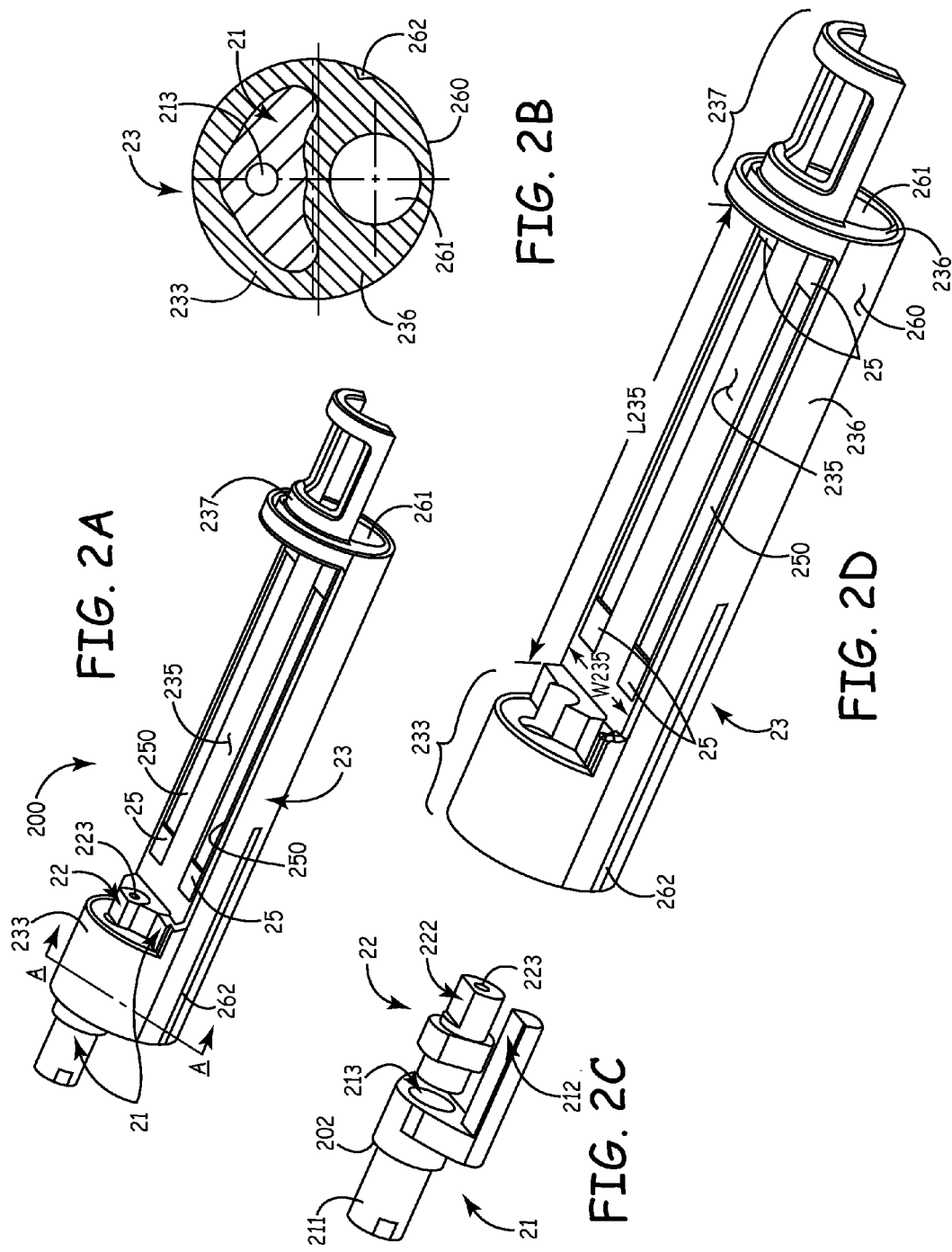

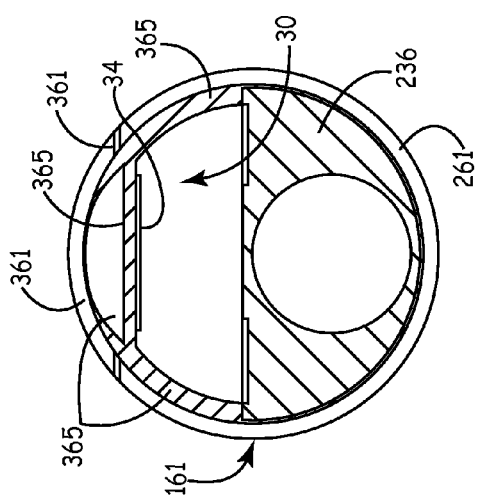
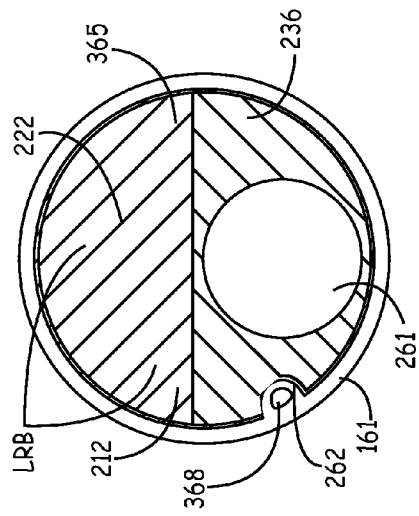
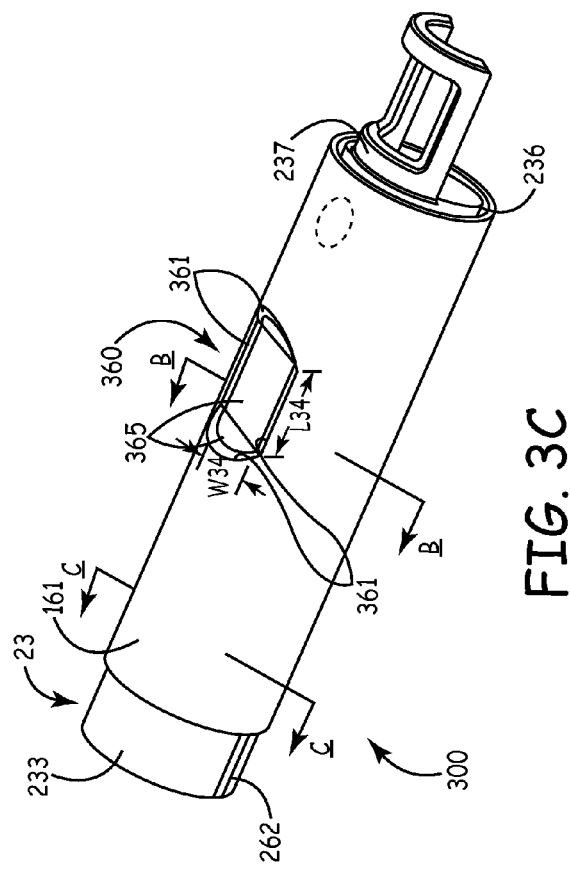

SENSOR ASSEMBLIES FOR IMPLANTABLE MEDICAL ELECTRICAL LEADS

TECHNICAL FIELD

The present disclosure pertains to implantable medical devices and more particularly to implantable medical electrical lead assemblies.

BACKGROUND

Implantable systems for cardiac rhythm management often employ medical electrical leads extending into the venous blood stream and being coupled to a surface of the heart. Typically, a medical electrical lead includes one or more electrodes for stimulating the heart and sensing electrical activity of the heart. In order to provide better management of cardiac conditions, the lead may also include a physiological sensor. The inclusion, on a single lead body, of electrodes, for stimulation and sensing, along with the physiological sensor poses some challenges for conductor routing in order to maintain a low profile for the lead body, without jeopardizing electrical isolation.

BRIEF DESCRIPTION OF THE DRAWINGS

The following drawings are illustrative of particular embodiments and are not intended to limit the scope of the invention. The drawings are not to scale (unless so stated) and are intended for use in conjunction with the explanations in the following detailed description. Embodiments will hereinafter be described in conjunction with the appended drawings, wherein like numerals denote like elements.

FIG. 2A is a perspective view of a mounting platform assembly for a sensor, according to some embodiments.

FIG. 2B is a section view through section line A-A of FIG. 2A.

FIGS. 2C-D are perspective views of portions of the assembly shown in FIG. 2A.

FIG. 3C is a perspective view of the sensor assembly, according to some embodiments.

FIGS. 3D-E are section views through section lines B-B and C-C, respectively, of FIG. 3C.

DETAILED DESCRIPTION

The following detailed description is exemplary in nature and is not intended to limit the scope, applicability, or configuration of the invention in any way. Rather, the following description provides practical illustrations for implementing exemplary embodiments. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1:
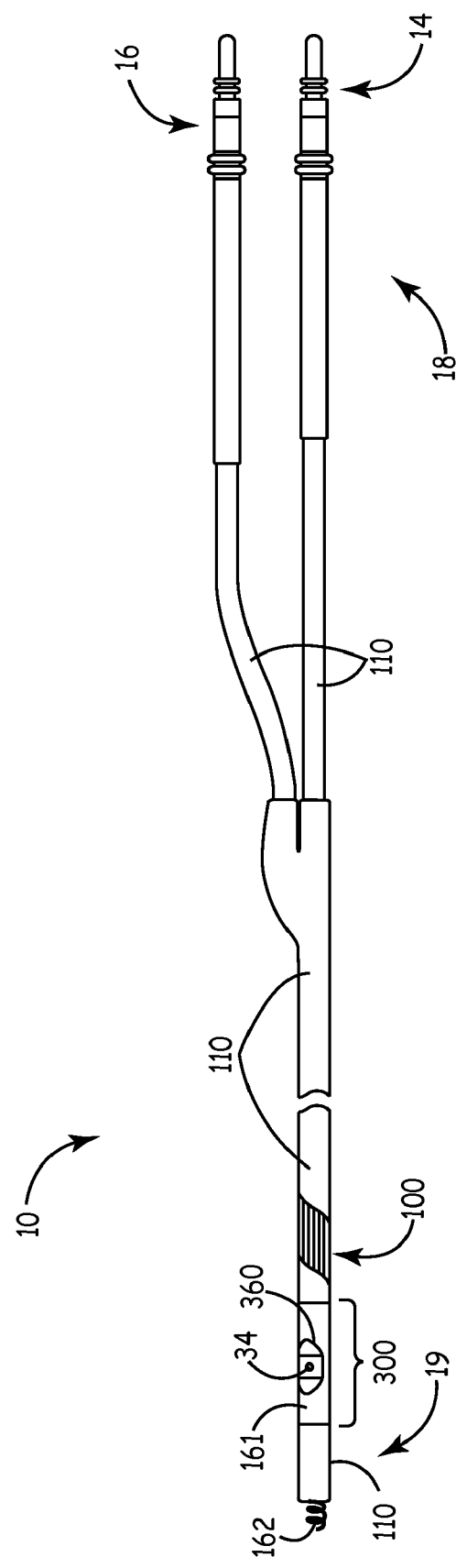
FIG. 1 is a plan view of medical electrical lead including a sensor assembly, according to some embodiments.
Figure 3A:
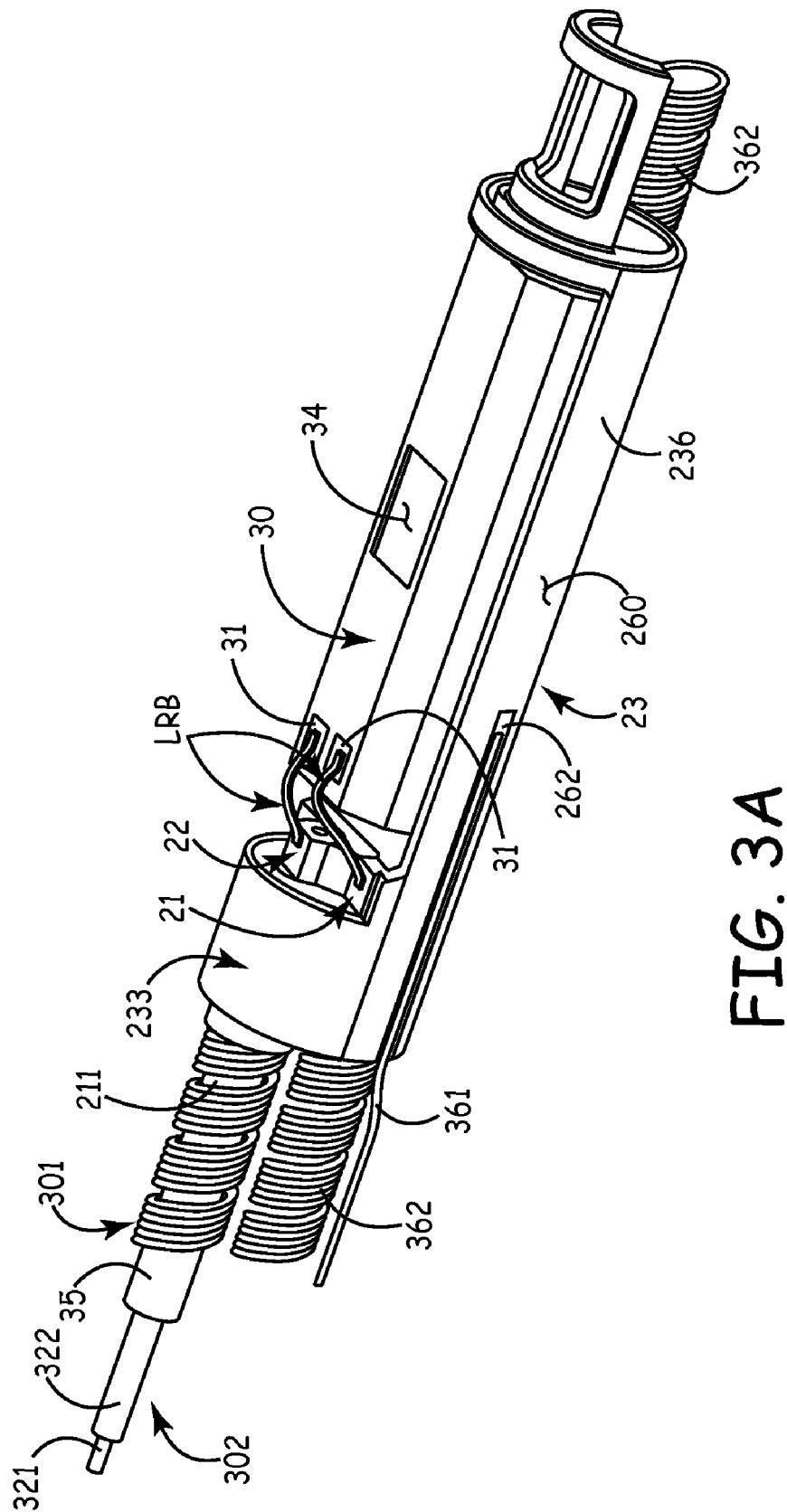
FIG. 3A is a perspective view of a portion of the medical electrical lead, that includes the sensor assembly, according to some embodiments.
Figure 3B:
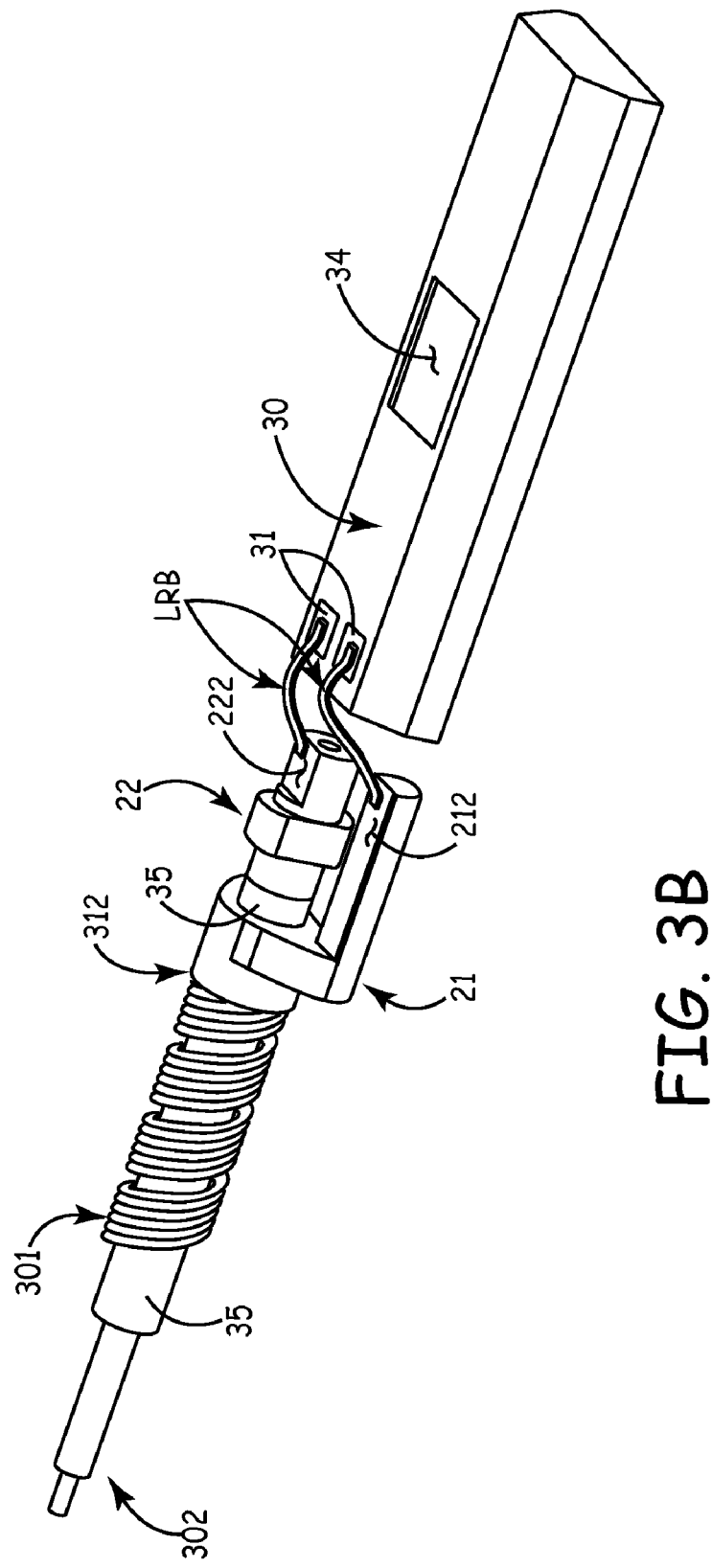
FIG. 3B is a perspective view of the portion shown in FIG. 3A, wherein an insulative body of the sensor assembly is removed to better show conductive inserts of the mounting platform assembly.

FIG. 1 is a plan view of medical electrical lead 10 including a physiological sensor assembly 300. FIG. 1 illustrates lead 10 including an insulative lead body 110 extending between a pair of connectors 14, 16, at a proximal end 18, and sensor assembly 300; lead body 110 further extends distally, from sensor assembly 300, to a distal end 19, from which a helix electrode 162 is shown extending. FIG. 1 further illustrates sensor assembly 300 including an electrode 16, which extends thereabout and includes an aperture 360 to expose an active surface 34 of a physiological sensor 30, which is shown in FIGS. 3A-B.

Connectors 14, 16 are configured for electrical coupling with an implantable medical device and may conform to an industry standard, for example IS-1. A plurality of isolated conductors extend within lead body 110, and that each of a pair of the conductors couples each contact of one of connectors 14, 16 to a respective electrode 16, 162, and each of another pair of the conductors couples each contact of another of connectors 14, 16 to sensor assembly 300.

Sensor assembly 300 includes a mounting assembly to facilitate integration of sensor 30 into lead body 110, for example, a mounting platform assembly 200, which is shown in FIGS. 2A-D. FIG. 2A is a perspective view of mounting platform assembly 200, according to some embodiments. FIG. 2A illustrates platform assembly 200 including an insulative body 23, a first conductive insert 21 and a second conductive insert 22, wherein first and second inserts 21, 22 extend within and are surrounded by a proximal portion 233 of insulative body 23. According to preferred embodiments, insulative body 23 is formed from a relatively rigid, biocompatible and biostable plastic, such as Polyetheretherketone (PEEK), and conductive inserts 21, 22 are formed from a biocompatible and biostable metal, such as titanium; an insert molding process is preferably employed to form platform assembly 200. With reference to FIG. 2C, which is a perspective view of conductive inserts 21, 22, having insulative body 23 removed, it may be seen that conductive inserts 21, 22 are spaced apart from one another to be electrically isolated from one another within proximal portion 233 of insulative body 23. (Body 23 is shown in FIG. 2D, having inserts 21, 22 removed.) FIGS. 2A and 2C further illustrate first conductive insert 21 including a first, conductor-coupling end 211, a second, sensor-coupling end 212 and a longitudinally extending lumen 213, and second conductive insert 22 including a longitudinally extending lumen 223 and a sensor-coupling end 222. Couplings to conductive inserts 21, 22 will be described below, in conjunction with FIGS. 3A-B.

FIGS. 2A and 2D illustrate insulative body 23 further including a mounting surface 235 for a sensor, wherein mounting surface 235 extends from proximal portion 233 to a distal portion 237 of insulative body 23. Distal portion 237 is shown having an exemplary configuration for joining to a distal portion of lead body 110, which extends between sensor assembly 300 and electrode 162 (FIG. 1); the distal portion of lead body 110 and a junction thereof with insulative body 23 may take on any suitable configuration so as not to limit embodiments of the present invention. According to the illustrated embodiment, mounting surface 235 includes a pair of longitudinally extending recesses 250 in which an agent 25, for example, silicone medical adhesive, is received in order to attach a bottom surface of a sensor, for example, sensor 30 shown in FIG. 3A, to mounting surface 235. According to some exemplary embodiments, a depth of each recess 250 is approximately 0.002 inch. It should be noted that, according to alternate embodiments, recesses 250 need not be included in mounting surface 235, or a single recess may be included, and that, if included, one or more recesses may be shaped and oriented in an suitable manner, not limited to the illustrated embodiment. Furthermore, the amount and extent of agent 25 may be varied from that shown.

Referring now to FIG. 2B, which is a section view through section line A-A of FIG. 2A, in conjunction with FIG. 2D, insulative body 23 further includes a lumen 261, which extends longitudinally through a sidewall 236 of insulative body 23, which sidewall 236 extends alongside mounting surface 235. According to the illustrated embodiment, lumen 261 forms an enclosed channel, for example, for a conductor, for example, conductor 362, which is shown in FIG. 3A and, according to some preferred embodiments, extends distally from sensor assembly 300 to couple with helix electrode 162 (FIGS. 1 and 3A). Sidewall 236 surrounding lumen 261 is sufficiently thick, for example, having a minimum thickness of approximately 0.002 inch, to provide stable electrical isolation for conductor 362, and lumen 261 is preferably sized to slidably accommodate conductor 362, so as not to impair a transfer of torque along conductor 362, for example, between a connector pin of one of connectors 14, 16, to which conductor 362 is coupled, and helix electrode 162; those skilled in the art understand that the transfer of torque extends helix electrode 162, for example, to fix electrode 162 to the surface of the heart. According to some exemplary embodiments, lumen 261 has an inner diameter of approximately 0.04 inch.

FIG. 3A is a perspective view of a portion of lead 10, which portion includes sensor assembly 300, according to some embodiments of the present invention. FIG. 3A illustrates sensor 30, which is mounted on mounting surface 235 of platform assembly 200 (FIG. 2A), a first pair of conductors 301, 302, of the plurality of conductors, which extends within lead body 110 to one of connectors 14, 16 (FIG. 1), and a second pair of conductors 361, 362 of the plurality of conductors, which extend to the other of connectors 14, 16. According to the illustrated embodiment: conductor 301 is formed from a plurality of coiled wire filars and is coupled to first conductive insert 21; conductor 302 is formed from a cabled bundle of wires 321 enclosed within an insulative jacket 322 and is coupled to second conductive insert 22; conductor 361 is similar to conductor 302 and extends within a groove 262 formed in sidewall 236 of insulative body 23 for coupling with electrode 161, which will be described in conjunction with FIGS. 3D and 3F; and conductor 362 is similar to conductor 301 and extends through lumen 261 of insulative body 23, as previously described. Those skilled in the art will appreciate that there are a number of suitable configurations for lead body 110 to provide the necessary electrical isolation for each of conductors 301, 302, 361, 362 extending therein. Wires of each of conductors 301, 302, 361, 362 may be formed from MP35N alloy, which is known to those skilled in the art, and insulative jackets of conductors 302, 361 may be formed from a fluoropolymer, such as PTFE or ETFE, known to those skilled in the art.

FIG. 3A further illustrates a pair of laser ribbon bonds LRB, each electrically coupling one of contacts 31 of sensor 30 to a corresponding conductive insert 21, 22; according to the illustrated embodiment, sensor-coupling ends 212 and 222 of inserts 21 and 22, respectively, each include an approximately flat surface for the corresponding laser ribbon bond LRB. Couplings between conductive inserts 21, 22 and conductors 301, 302 will be described in greater detail below, in conjunction with FIG. 3B. According to some preferred embodiments, sensor 30 comprises a microelectromechanical systems (MEMS) capacitive pressure transducer, which includes a hermetically sealed pressure cavity contained by an insulative sidewall, which includes active surface 34, extending over a portion thereof, which portion is formed to be a pressure sensitive diaphragm, for example, being thinner than other portions of the sidewall; at least two spaced apart electrode plates, one of which is attached to an inner side of the diaphragm, and electronics are located within the cavity; the electronics may be coupled to contacts 31 via feedthroughs extending through the sidewall of the pressure cavity. An example of a MEMS pressure transducer is described in pre-grant patent publications 2007/0107524 and 2007/0199385, which are hereby incorporated by reference. With reference back to FIG. 2D, according to some exemplary embodiments of the present invention, wherein sensor 30 comprises a MEMS pressure transducer, a length L235 of mounting surface 235 is between approximately 0.265 inch and approximately 0.275 inch, and a width W235 of surface 235 is between approximately 0.09 inch and approximately 0.1 inch. Of course, it should be appreciated that embodiments of the present invention may facilitate the incorporation of other types of physiological sensors, for example, optical, chemical, etc., into lead body 110, and mounting surface 235 may be appropriately dimensioned according to a footprint of the desired type of sensor.

FIG. 3B is a perspective view of the portion of lead 10 shown in FIG. 3A, wherein insulative body 23 is removed to better show conductive inserts 21, 22, according to some embodiments. FIG. 3B illustrates conductor 301, which extends coaxially about conductor 302, mounted on first conductor-coupling end 211 of first conductive insert 21 and abutting a shoulder 202 of conductive insert 21, where a laser weld 312 electrically couples conductor 301 to insert 21. Alternatively, a crimp may be formed between conductor 301 and end 211 of insert 21, according to methods known to those skilled in the art. FIG. 3B further illustrates conductor 302 extending within an optional insulative tubing 35, about which conductor 301 extends and which may extend proximally along a significant length of lead body 110; although not shown, it should be appreciated that conductor 322 further extends into proximal portion 233 of insulative body 23 to couple with second conductive insert 22, for example, via a laser weld.

FIG. 3C is a perspective view of sensor assembly 300, according to some embodiments; and FIGS. 3D-E are section views through section lines B-B and C-C, respectively, of FIG. 3C. FIGS. 3C-E illustrate electrode 161 extending around sensor 30 and sidewall 236 of insulative body 23 such that proximal and distal portions 233, 237 extend from either end of electrode 161, and aperture 360 of electrode 161 is positioned to expose active surface 34 of sensor 30 therethrough. According to the illustrated embodiment, an insulative sealing material 365 extends over active surface 34 and around sensor 30, within electrode 161, to prevent fluid ingress, from an environment in which sensor assembly 300 may be implanted, and to electrically isolate conductive elements, for example, laser ribbon bonds LRB and first and second conductive inserts 21, 22, of sensor assembly 300 from one another. According to alternate embodiments, sealing material 365 does not extend over active surface, but at least about a perimeter 361 of aperture 360. Preferably, sealing material 365 substantially fills a space that surrounds sensor 30, within electrode 161, between proximal portion 233, distal portion 237 and mounting surface 235 of insulative body 23.

According to some embodiments, a minimum thickness of sealing material 365 between an inner surface of electrode 161 and sensor 30 is approximately 0.003 inch. According to some exemplary embodiments, an inner diameter of electrode 161 is between approximately 0.081 inch and approximately 0.110 inch. With reference to FIGS. 3D-E, in conjunction with FIG. 2D, it may be appreciated that sidewall 236 includes an arcuate surface 260 for supporting electrode 161. According to some exemplary embodiments, sealing material 365 comprises liquid silicone rubber which may be injected between electrode 161 and sensor 30 through one or more ports located in insulative body 23 (not shown) and/or through a port (shown with a dashed line in FIG. 3C) located in electrode 161. For those embodiments, wherein active surface 34 is of a pressure sensitive diaphragm, it may be necessary to inject sealing material 365 away from the diaphragm in order to avoid compromising sensor 30.

FIG. 3E further illustrates a coupling feature 368, formed along an inner surface of electrode 161 and positioned within groove 262, which is formed in arcuate surface 260 of sidewall 236. As previously described, in conjunction with FIG. 3A, conductor 361 extends within groove 262 for coupling with electrode 161; and, although not shown, those skilled in the art will appreciate that conductor 361 may be staked or crimped within coupling feature 368 of electrode 161.

Finally, an outline of assembly steps, for some embodiments of the present invention, may be as follows. In an initial assembly step, mounting platform assembly 200, as shown in FIG. 2A, is insert molded. Molded assembly 200 may be cleaned and/or plasma treated prior to applying agent 25 into recesses 250 of mounting surface 235, and then sensor 30 is attached thereto, as shown in FIG. 3A. After sensor 30 is attached, laser ribbon bonds LRB are formed to couple sensor contacts 31 to respective sensor-coupling ends 212, 222 of conductive inserts 21, 22, respectively, and conductor 302 is coupled to second conductive insert 22. Electrode 161 may then be mounted around molded assembly 200 and sensor 30, as shown in FIG. 3C. Conductor 361 (FIG. 3A) may have been coupled to electrode 161 either before or after mounting electrode 161. In a final step, prior to integration into lead body 110, sealing material 365 is injected between electrode 161 and sensor 30, as previously described, and allowed to cure.

In the foregoing detailed description, the invention has been described with reference to specific embodiments. However, it may be appreciated that various modifications and changes can be made without departing from the scope of the invention as set forth in the appended claims.

The invention claimed is:

1. A mounting platform assembly for an implantable sensor, the assembly comprising:
    an insulative body formed from a biocompatible plastic, the body including a proximal portion and a mounting surface for the sensor, the mounting surface extending distally from the proximal portion;
    a first conductive insert extending within and being surrounded by the proximal portion of the insulative body, the first insert including a first, conductor-coupling end extending proximally from the insulative body and a second, sensor-coupling end extending distally from the proximal portion of the insulative body to be exposed exterior to the mounting surface of the insulative body; and
    a second conductive insert extending within and being surrounded by the proximal portion of the insulative body, and further being spaced apart and electrically isolated from the first conductive insert, the second conductive insert including a sensor-coupling end extending distally from the proximal portion of the insulative body to be exposed exterior to the mounting surface of the insulative body.

2. The platform assembly of claim 1, wherein:
    the insulative body further includes a sidewall extending alongside the mounting surface and a lumen extending through the sidewall and longitudinally along the mounting surface; and
    the lumen is laterally offset from the mounting surface and from the first and second conductive inserts.

3. The platform assembly of claim 1, wherein:
    the insulative body further includes a sidewall extending alongside the mounting surface; and
    the sidewall includes an arcuate surface facing away from the mounting surface, for supporting an electrode.

4. The platform assembly of claim 3, wherein the sidewall of the insulative body further includes a groove formed in the arcuate surface thereof, the groove to accommodate an elongate conductor extending therein for coupling to the electrode, when the electrode is supported by the arcuate surface.

5. The platform assembly of claim 1, wherein the mounting surface of the insulative body includes at least one longitudinally extending recess formed therein, the at least one recess to receive an agent for attaching the sensor to the mounting surface.

6. The platform assembly of claim 1, wherein the first, conductor-coupling end of the first conductive insert is sized to mount a coiled conductor thereabout.

7. The platform assembly of claim 1, wherein the second, sensor-coupling end of the first conductive insert includes an approximately flat surface for a laser ribbon bond to couple the sensor to the first conductive insert, when the sensor is mounted on the mounting surface of the insulative body.

8. The platform assembly of claim 1, wherein the sensor-coupling end of the second conductive insert includes an approximately flat surface for a laser ribbon bond to couple the sensor to the first conductive insert, when the sensor is mounted on the mounting surface of the insulative body.

9. The platform assembly of claim 1, wherein the biocompatible plastic of the insulative body is insert molded about the first and second conductive inserts.

10. The platform assembly of claim 1, wherein the biocompatible plastic of the insulative body comprises PEEK.

11. An implantable sensor assembly comprising:
    an insulative body formed from a biocompatible plastic, the body including a proximal portion and a mounting surface, the mounting surface extending distally from the proximal portion;
    a first conductive insert extending within and being surrounded by the proximal portion of the insulative body, the first insert including a first, conductor-coupling end extending proximally from the insulative body and a second, sensor-coupling end extending distally from the proximal portion of the insulative body;
    a second conductive insert extending within and being surrounded by the proximal portion of the insulative body, and further being spaced apart and electrically isolated from the first conductive insert, the second conductive insert including a sensor-coupling end extending distally from the proximal portion of the insulative body; and
    a sensor mounted on the mounting surface of the insulative body and being coupled to the sensor-coupling ends of the first and second conductive inserts, the sensor including an active surface facing away from the mounting surface of the insulative body.

12. The sensor assembly of claim 11, wherein:
the insulative body further includes a sidewall extending alongside the mounting surface and a lumen extending through the sidewall and longitudinally along the mounting surface; and
the lumen is laterally offset from the mounting surface and from the first and second conductive inserts.

13. The sensor assembly of claim 11, further comprising:
an electrode extending around the sensor and the insulative body, the electrode including an aperture positioned to expose the active surface of the sensor therethrough; and
an insulative sealing material extending at least about a perimeter of the aperture of the electrode and within the electrode;
wherein the insulative body further includes a sidewall extending alongside the mounting surface, the sidewall including an arcuate surface facing away from the mounting surface, for supporting the electrode.

14. The sensor assembly of claim 13, wherein the sealing material substantially fills a space, around the sensor, enclosed between the electrode and the mounting surface.

15. The sensor assembly of claim 13, wherein the sidewall of the insulative body further includes a groove formed in the arcuate surface thereof, the groove to accommodate an conductor extending therein for coupling to the electrode.

16. The assembly of claim 11, wherein the sensor is attached to the mounting surface of the insulative body by an agent located within at least one recess formed within the mounting surface.

17. The assembly of claim 11, wherein the sensor comprises a pressure transducer and the active surface is of a pressure-sensitive diaphragm.

18. A medical electrical lead comprising:
an insulative lead body;
a plurality of elongate conductors electrically isolated from one another and extending within the lead body; and
a sensor assembly attached to the lead body, the sensor assembly comprising:
an insulative body formed from a biocompatible plastic, the body including a proximal portion attached to the lead body and a mounting surface extending distally from the proximal portion;
a first conductive insert extending within and being surrounded by the proximal portion of the insulative body, the first insert including a first end extending proximally from the insulative body and being coupled to a first conductor of the plurality of elongate conductors;
a second conductive insert extending within and being surrounded by the proximal portion of the insulative body, and further being spaced apart and electrically isolated from the first conductive insert, the second conductive insert being coupled to a second conductor of the plurality of elongate conductors;
a sensor mounted on the mounting surface of the insulative body and being coupled to the first and second conductive inserts, the sensor including an active surface facing away from the mounting surface of the insulative body;
an electrode extending around the sensor and the insulative body, the electrode including an aperture positioned to expose the active surface of the sensor therethrough; and
an insulative sealing material extending at least about a perimeter of the aperture of the electrode and within the electrode.

19. The lead of claim 18, wherein:
the insulative body of the sensor assembly further includes a sidewall extending alongside the mounting surface and a lumen extending through the sidewall along the mounting surface;
the lumen is laterally offset from the mounting surface and from the first and second conductive inserts; and
a third conductor of the plurality of elongate conductors extends within the lumen, being electrically isolated from the sensor.

20. The lead of claim 19, further comprising an active fixation electrode coupled to the third conductor.

21. The lead of claim 18, wherein:
the insulative body of the sensor assembly further includes a sidewall extending alongside the mounting surface, the sidewall including an arcuate surface facing away from the mounting surface, for supporting the electrode, and a groove formed in the arcuate surface; and
a third conductor of the plurality of elongate conductors extends within the groove to couple with the electrode.

22. The lead of claim 18, wherein the sealing material of the pressure sensor assembly substantially fills a space, around the sensor, enclosed between the electrode and the mounting surface.

23. The lead of claim 18, wherein the sensor is attached to the mounting surface of the insulative body of the sensor assembly by an agent located within at least one recess formed within the mounting surface.

24. The lead of claim 18, wherein the sensor comprises a pressure transducer and the active surface is of a pressure-sensitive diaphragm.

25. The lead of claim 18, wherein the sensor assembly further comprises first and second laser bonded ribbons, the first laser bonded ribbon coupling the sensor to the first conductive insert and the second laser bonded ribbon coupling the sensor to the second conductive insert.

26. The lead of claim 18, wherein the first and second conductive inserts of the sensor assembly each include a sensor-coupling end extending distally from the proximal portion of the insulative body.

* * * * *